United States Patent
Remick (10) Patent No.: US 12,102,610 B2
(45) Date of Patent: Oct. 1, 2024

(54) TREPROSTINIL SALT

(71) Applicant: Eli Lilly and Company, Indianapolis, IN (US)

(72) Inventor: David Michael Remick, Fishers, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 824 days.

(21) Appl. No.: 17/274,883

(22) PCT Filed: Sep. 11, 2019

(86) PCT No.: PCT/US2019/050632
§ 371 (c)(1),
(2) Date: Mar. 10, 2021

(87) PCT Pub. No.: WO2020/060823
PCT Pub. Date: Mar. 26, 2020

(65) Prior Publication Data
US 2022/0047535 A1    Feb. 17, 2022

Related U.S. Application Data

(60) Provisional application No. 62/732,799, filed on Sep. 18, 2018.

(51) Int. Cl.
A61K 31/192   (2006.01)
A61K 38/28    (2006.01)
C07C 59/72    (2006.01)

(52) U.S. Cl.
CPC ............ *A61K 31/192* (2013.01); *A61K 38/28* (2013.01); *C07C 59/72* (2013.01); *C07B 2200/13* (2013.01); *C07C 2603/16* (2017.05)

(58) Field of Classification Search
CPC .... A61K 38/28; A61K 31/5575; C07C 59/72; C07C 2603/16; C07C 51/43; C07C 59/68; C07B 2200/13; A61P 3/10; A61P 9/08
See application file for complete search history.

(56) References Cited

U.S. PATENT DOCUMENTS

| | | |
|---|---|---|
| 4,306,075 A | 12/1981 | Aristoff |
| 5,153,222 A | 10/1992 | Tadepalli et al. |
| 5,981,594 A | 11/1999 | Okamoto et al. |
| 6,756,033 B2 | 6/2004 | Cloutier et al. |
| 6,765,117 B2 | 7/2004 | Moriarty et al. |
| 6,809,223 B2 | 10/2004 | Moriarty et al. |

(Continued)

FOREIGN PATENT DOCUMENTS

| | | |
|---|---|---|
| EP | 0001124 A1 | 3/1979 |
| EP | 2500020 A1 | 9/2014 |

(Continued)

OTHER PUBLICATIONS

Blaise, S., et al., "Cathodal Iontophoresis of Treprostinil Induces a Sustained Increase in Cutaneous Blood Flux in Healthy Volunteers," J. Clin. Pharmacol., vol. 53, Issue 1, DD. 58-66 (2012).

(Continued)

*Primary Examiner* — Deborah D Carr
(74) *Attorney, Agent, or Firm* — Perry Woo (57) ABSTRACT

A novel salt of treprostinil and methods of its preparation and use are disclosed.

19 Claims, 4 Drawing Sheets

(56) References Cited

U.S. PATENT DOCUMENTS

| | | |
|---|---|---|
| 7,199,157 B2 | 4/2007 | Wade et al. |
| 7,417,070 B2 | 8/2008 | Phares et al. |
| 7,999,007 B2 | 8/2011 | Jeffs et al. |
| 8,252,839 B2 | 8/2012 | Phares et al. |
| 8,324,157 B2 | 12/2012 | Olsen et al. |
| 8,349,892 B2 | 1/2013 | Phares |
| 8,350,079 B2 | 1/2013 | Walsh |
| 8,461,393 B2 | 6/2013 | Sharma |
| 8,481,782 B2 | 7/2013 | Batra et al. |
| 8,497,393 B2 | 7/2013 | Batra et al. |
| 8,536,363 B2 | 9/2013 | Phares et al. |
| 8,563,614 B2 | 10/2013 | Wade et al. |
| 8,609,728 B2 | 12/2013 | Rothblatt et al. |
| 8,653,137 B2 | 2/2014 | Jeffs et al. |
| 8,658,694 B2 | 2/2014 | Jeffs et al. |
| 8,747,897 B2 | 6/2014 | Kidane et al. |
| 8,765,813 B2 | 7/2014 | Wade et al. |
| 9,050,311 B2 | 6/2015 | Phares et al. |
| 2005/0282901 A1 | 12/2005 | Phares et al. |
| 2009/0036465 A1 | 2/2009 | Roscigno et al. |
| 2009/0075976 A1 | 3/2009 | Verbeuren et al. |
| 2012/0004307 A1 | 1/2012 | Wade et al. |
| 2012/0010159 A1 | 1/2012 | Rothblatt et al. |
| 2012/0216801 A1 | 8/2012 | Olschewski et al. |
| 2013/0331593 A1 | 12/2013 | Mcgowan et al. |
| 2014/0018431 A1 | 1/2014 | Wade et al. |
| 2014/0193379 A1 | 7/2014 | Jeffs et al. |
| 2014/0275262 A1 | 9/2014 | Phares et al. |
| 2014/0275616 A1 | 9/2014 | Batra et al. |
| 2014/0323567 A1 | 10/2014 | Laing |
| 2015/0065423 A1 | 3/2015 | Laulicht et al. |
| 2015/0164834 A1 | 6/2015 | Cloutier et al. |
| 2016/0243064 A1* | 8/2016 | Trehan ............... A61K 31/5575 |
| 2017/0056478 A1* | 3/2017 | Akers ....................... A61P 3/10 |

FOREIGN PATENT DOCUMENTS

| | | |
|---|---|---|
| WO | 2003094956 A1 | 11/2003 |
| WO | 2005007081 A2 | 1/2005 |
| WO | 2010023666 A2 | 3/2010 |
| WO | 2010149772 A1 | 12/2010 |
| WO | 2012088607 A1 | 5/2012 |
| WO | 2012080362 A1 | 6/2012 |
| WO | 2015073314 A1 | 5/2015 |
| WO | 2015120457 A1 | 8/2015 |
| WO | 2015171484 A1 | 11/2015 |
| WO | 2018106632 A1 | 6/2018 |

OTHER PUBLICATIONS

Gille, A., et al., "Nicotinic Acid: Pharmacological Effects and Mechanisms of Action," Annu. Rev. Pharmacol. Toxicol., vol. 48, oo. 79-106 (2008).

Mathier, M., et al., "Subcutaneous Treprostinil in Pulmonary Arterial Hypertension: Practical Considerations," J. Heart Luna Transplant., vol. 29, DD. 1210-1217 (2010).

Mcswain, C., et al., "Dose Proportionality of Treprostinil Sodium Administered by Continuous Subcutaneous and Intravenous Infusion," J. Clin. Pharmacol., vol. 48, DD. 19-25 (2008).

Menon, R., et al., "Insulin Absorption Accelerated by a-Adrenergic Blockade at Injection Site," Diabetes Care, vol. 10, No. 4, DD. 470-472 (1987).

Moriarty, R., et al., "The Intramolecular Asymmetric Pauson-Khand Cyclization as a Novel and General Stereoselective Route to Benzindene Prostacyclins: Synthesis of UT-15 (Treprostinil)," J. Org. Chem, vol. 69, DD. 1890-1902 (2004).

NDA 21-272, RemodulinTM, Clinical Pharmacology & Biopharmaceutics Review(s), available at http://www.accessdata.fda.gov/drugsatfda_docs/nda/2002/21-272_Remodullin.cfm, pp. 1-112, (Jul. 31, 2002).

NDA 21-272, RemodulinTM, Medical Review, available at http://wwww.accessdata_fda.gov/drugsatfda_docs/nda/2002/21-272_Remodulin.ofm, pp. 1-195, (Jul. 31, 2002).

Owens, D., et al., "The Influence of Aprotinin on Regional Absorption of Soluble Human Insulin," Br. J. Clin. Pharmac., vol. 25, DD. 453-456 (1988).

REMODULIN® (treprostinil) Injection Package Insert, pp. 1-17, (May 2002).

Skoro-Sajer, Nika, et al., "Treprostinil for Pulmonary Hypertension," Vascular Health and Risk Management, Jan. 1, 2008, pp. 507-513.

Vora, J., et al., "Relationship Between Absorption of Radiolabeled Soluble Insulin, Subcutaneous Blood Flow, and Anthrooometrv," Diabetes Care, vol. 15, No. 11, DD. 1484-1493 (1992).

Wade, M., et al., "Absolute Bioavailability and Pharmacokinetics of Treprostinil Sodium Administered by Acute Subcutaneous Infusion," J. Clin. Pharmacol., vol. 44, oo. 83-88 (2004).

Waki, et. al., *Insulin Resistance in Endothelium and Aging*, Heart View; vol. 17, No. 4, p. 53(385)-60(392), 2013.

Whittle, B.J. et al., "Binding and activity of the prostacyclin receptor (IP) agonists, treprostinil and iloprost, at human prostanoid receptors: Treprostinil is a potent DP, and EP2 agonist," Biochemical Pharmacolonv, 84 (2012) 68-75.

Williams, G., et al., "Subcutaneous Aprotinin Causes Local Hyperaemia," Diabetologia, vol. 24, pp. 91-94 (1983).

Williams, G., et al., "Prostaglandin E1 Accelerates Subcutaneous Insulin Absorption in Insulin-Dependent Diabetic Patients," Diabetic Medicine, oo.109-113 (1984).

Patent Cooperation Treaty International Search Report pertaining to International Application No. PCT/US2019/050632; International Filing Date: Sep. 11, 2019; Date of Mailing: Nov. 4, 2019.

Patent Cooperation Treaty Written Opinion of the International Searching Authority pertaining to International Application No. PCT/US2019/018757; International Filing Date: Sep. 11, 2019; Date of Mailing: Nov. 4, 2019.

Hirayama, N., "Handbook for preparing organic compound crystals, Principle and know-how," 2008, Maruzen Publishing, Japan, 320 pages.

Kawaguchi, Y. et. al., "Drug and crystal polymorphism," Journal of Human Environmental Engineering, 2002, vol. 4, No. 2, p. 310-317.

* cited by examiner

TREPROSTINIL SALT

The present invention provides a novel salt of treprostinil and crystalline forms thereof.

Treprostinil (CAS No. 81846-19-7), the chemical name of which is (1R,2R,3aS,9aS)-[[2,3,3a,4,9,9a-Hexahydro-2-hydroxy-1-[(3S)-3-hydroxyoctyl]-1H-benz[f]inden-5-yl]oxy] acetic acid has the following formula:

It has a molecular weight of 390.5 and a molecular formula of $C_{23}H_{34}O_5$.

Treprostinil is the active ingredient in Remodulin®, Tyvaso® and Orenitran™, which are indicated for the treatment of pulmonary arterial hypertension to diminish symptoms associated with exercise (Remodulin®) and to improve exercise ability (Tyvaso® and Orenitran™). Tyvaso® and Orenitran™ are, respectively, inhalation and oral dosage forms, and Remodulin® is indicated for subcutaneous or intravenous use as a continuous infusion.

Currently approved formulations of treprostinil include the sodium salt and free acid, but the physical and chemical stability of these forms of treprostinil, are sensitive to the conditions in which they are tested, stored and used, particularly in terms of thermal stability and hygroscopicity, and thus require specific processes and equipment, including rigid temperature and humidity controls.

Thus, there is a need for improved forms of treprostinil with superior properties that do not require such rigid environmental controls.

Previous efforts to identify improved forms of treprostinil have been undertaken. For example, U.S. Pat. No. 8,252,839 describes a diethanolamine salt of treprostinil, and states that the compounds described therein have enhanced oral bioavailability to the free acid or salt forms. Similarly, U.S. Pat. No. 8,350,079 describes a monohydrate form of treprostinil made from diethanolamine salt that is stated to provide improved stability at room temperature. Finally, U.S. Pat. No. 9,701,611 describes Group IA or IIA metal salts of treprostinil and states that such salts have improved solubility.

Nevertheless, the need remains for new forms of treprostinil with superior physical properties, and which may be handled, stored and used in analytical and/or manufacturing settings without the need for unduly burdensome environmental controls.

Due to the sensitivity of treprostinil free acid and treprostinil sodium salt—the two most common physical forms of treprostinil—to environmental conditions, efforts were undertaken to identify a form of treprostinil with superior physical properties. It was discovered that the erbumine salt of treprostinil has surprisingly superior physical properties, including reduced sensitivity to moisture and improved thermal stability. The improved thermal stability of the erbumine salt allows for improved performance under drying conditions, and simplifies shipping, storage and analysis.

In one aspect, the present invention provides treprostinil erbumine salt having the following structure.

In another embodiment, the present invention provides treprostinil erbumine salt in crystalline form characterized by an X-ray powder diffraction (XRD) pattern obtained from CuKα source (λ=1.54060 Å) which comprises peaks at 5.1° and at least one of 10.2°, 20.5° and 6.8° with a tolerance for the diffraction angles of 0.2°.

In another embodiment, the present invention provides treprostinil erbumine salt in crystalline form characterized by an XRD pattern obtained from CuKα source (λ=1.54060 Å) which comprises peaks at 5.1° and at each of 10.2°, 20.5° and 6.8° with a tolerance for the diffraction angles of 0.2°.

In another embodiment, the present invention provides treprostinil erbumine salt in crystalline form characterized by an XRD pattern obtained from CuKα source (λ=1.54060 Å) which comprises peaks at 5.1°, 10.2°, 20.5°, 6.8° and at least one of 13.7°, 14.5°, 16.3°, 18.7°, 19.6° and 21.5° with a tolerance for the diffraction angles of 0.2°.

In another embodiment, the present invention provides treprostinil erbumine salt in crystalline form characterized by an XRD pattern obtained from CuKα source (λ=1.54060 Å) which comprises peaks at 5.1°, 10.2°, 20.5°, 6.8°, 13.7°, 14.5°, 16.3°, 18.7°, 19.6° and 21.5° with a tolerance for the diffraction angles of 0.2°.

In another aspect, the present invention provides a pharmaceutical composition comprising any of the above-described treprostinil erbumine salts and at least one of a pharmaceutically acceptable carrier, excipient or diluent.

In certain embodiments, the pharmaceutical composition further comprises an additional substance with pharmacological activity. In certain embodiments, the additional substance with pharmacological activity is an insulin. In certain embodiments, the insulin is insulin lispro.

In another aspect, the present invention provides a method of treating or preventing hyperglycemia in a patient in need thereof comprising administering a therapeutically effective amount of a pharmaceutical composition comprising any of the above-described treprostinil erbumine salts, at least one of a pharmaceutically acceptable carrier, excipient or diluent, and an insulin.

In another aspect, the present invention provides a method of treating or preventing hypertension in a subject in need thereof comprising administering a pharmaceutically effective amount of any of the above-described treprostinil erbumine salts.

In another aspect, the present invention provides use of any of the above-described treprostinil erbumine salts in treating or preventing hypertension.

In another aspect, the present invention provides use of any of the above-described treprostinil erbumine salts in the manufacture of a medicament for treating or preventing hypertension.

In another aspect, the present invention provides use of any of the above-described treprostinil erbumine salts as a reference standard for determining the potency of treprostinil in a composition comprising treprostinil.

In another aspect, the present invention provides a method of manufacturing the treprostinil erbumine salt of any of the above-described embodiments comprising:
a) contacting treprostinil free acid to an antisolvent to create a suspension;
b) contacting the suspension to a solution comprising t-butylamine (erbumine); and
c) isolating the resulting solid treprostinil erbumine salt.

As noted above, treprostinil is the approved active agent in several products approved for the treatment of pulmonary arterial hypertension. Treprostinil has also been described for use in other therapeutic areas, including improving kidney functions (see U.S. Pat. No. 7,199,157), treating ischemic lesions (see U.S. Pat. No. 8,765,813), treating neuropathic diabetic foot ulcers (see U.S. Pat. No. 8,563,614), treating intersitial lung disease and asthma (U.S. Application Number 2014018431), and treatment of vasculopathy (see U.S. Application Number 2014193379).

Treprostinil has also been described as being capable of accelerating the time action profile of an insulin (see U.S. Pat. No. 9,439,952). When used herein, the term "insulin" refers to human insulin, bovine insulin, porcine insulin, or any analog or derivative thereof, including the rapid acting acting insulin analogs insulin lispro, insulin aspart and insulin glulisine.

Erbumine (CAS number 107133-36-8), which may also be referred to as t-butylamine, has the formula $(CH_3)_3CNH_2$, a molar mass of 73.14, and the following structure:

The treprostinil erbumine salt of the present invention has the following structure:

It will be recognized that the treprostinil erbumine salt of the present invention may be suitable for use in any of the contexts described above.

In addition, in view of its reduced sensitivity to moisture, the treprostinil erbumine salt of the present invention is also useful as a reference standard for use in analyzing a sample comprising any form of treprostinil.

EXAMPLES

Preparation of 2-[[(1R,2R,3aS,9aS)-2-hydroxy-1-[(3S)-3-hydroxyoctyl]-2,3,3a,4,9,9a-hexahydro-1H-cyclopenta[g]naphthalen-5-yl]oxy]acetic acid t-butylamine (Treprostinil erbumine)

Treprostinil free acid (100 mg) is added to acetone (2 mL) while stirring at room temperature. The suspension is heated to 50° C. In a separate vessel, t-butylamine (26 mg, 1.4 equiv) is mixed with acetone (1 mL). The base solution is added dropwise and the suspension becomes a solution for a few minutes, after which time a suspension forms. Acetone (1 mL) is added and mixing continues for 2 hours. The mixture is stirred and cooled overnight. The white solid is isolated by vacuum filtration on Whatman paper. The resulting cake of white solid is air dried in place to give 99 mg (83% yield) of the title compound.

X-Ray Powder Diffraction (XRD) of Crystalline Treprostinil Erbumine

The XRD patterns of crystalline solids are obtained on a Bruker D4 Endeavor X-ray powder diffractometer, equipped with a CuKα source λ=1.54060 Å and a Vantec detector, operating at 35 kV and 50 mA. The sample is scanned between 4 and 40° in 2θ, with a step size of 0.008° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, are adjusted based on NIST 675 standard peaks at 8.853 and 26.774° 2θ.

A prepared sample of the crystalline erbumine salt is analyzed by XRD as described above and is characterized by an XRD pattern as having diffraction peaks as described in Table 1 below, and in particular having peaks at 5.1° in combination with one or more of the peaks selected from the group consisting of 10.2°, 20.5°, and 6.8°; with a tolerance for the diffraction angles of 0.2°.

TABLE 1

XRD peaks of crystalline treprostinil erbumine

| Peak | Angle (°2-Theta) +/−0.2° | Relative Intensity (% of most intense peak) |
|---|---|---|
| 1 | 5.1 | 100 |
| 2 | 6.8 | 36.8 |
| 3 | 10.2 | 55.7 |
| 4 | 13.7 | 34.3 |
| 5 | 14.5 | 18.1 |
| 6 | 16.3 | 17.2 |
| 7 | 18.7 | 15.2 |
| 8 | 19.6 | 18.8 |
| 9 | 20.5 | 42.8 |
| 10 | 21.5 | 17.2 |

Thermal Characterization of Treprostinil Erbumine Salt and Free Acid

The thermal stability of samples of treprostinil erbumine salt, prepared as described above, and treprostinil free acid, purchased from a chemical supply company, are analyzed through thermal gravimetric analyses (TGA) performed on a TA Instruments TGA-Q5000 thermal gravimetric analyzer and differential scanning calorimetry (DSC) performed on a TA Instruments Q2000 differential scanning calorimeter.

Figure 1:
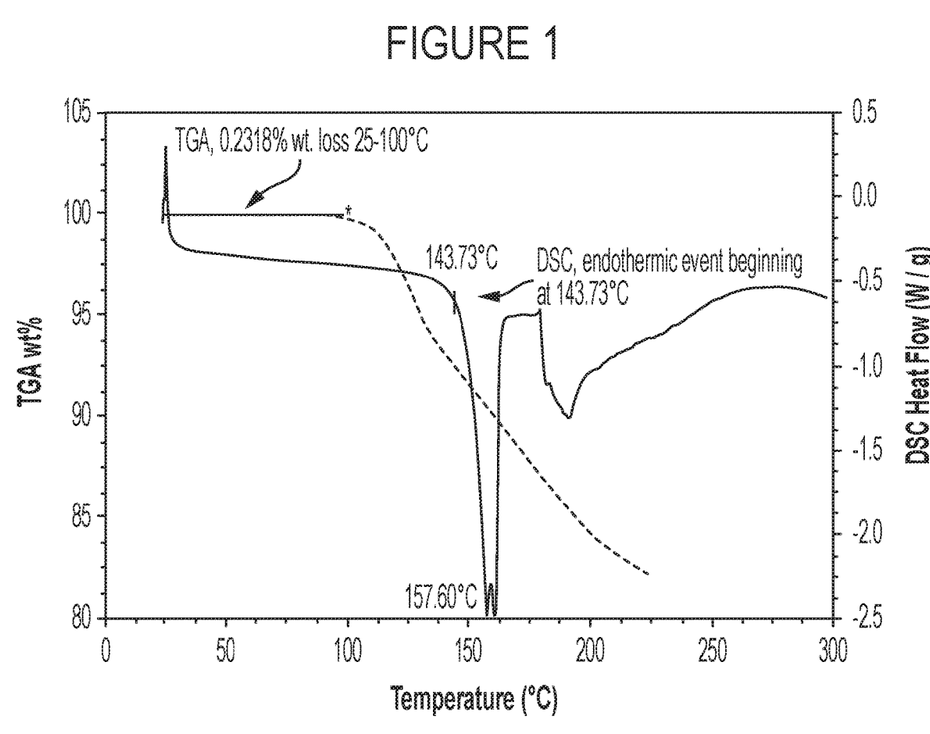
FIG. 1: Overlay of the thermal gravimetric analysis (TGA) and differential scanning calorimetry (DSC) thermograms of treprostinil erbumine.
Figure 2:
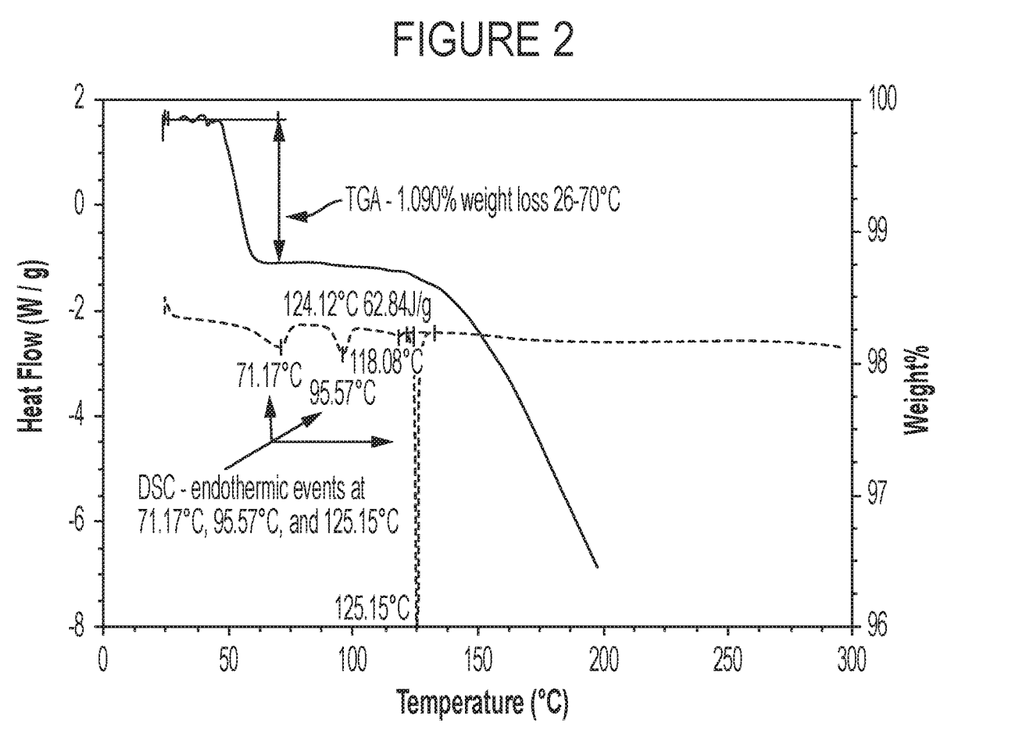
FIG. 2: Overlay of the thermal gravimetric analysis (TGA) and differential scanning calorimetry (DSC) thermograms of treprostinil free acid.

FIGS. 1 (erbumine salt) and 2 (free acid) show overlays of the TGA thermograms from 25-225° C. and the DSC thermograms from 25-300° C. The TGA data show that weight loss between 25-100° C. is 0.2318% for the erbumine salt and 1.090% between 26-70° C. for the free acid. DSC data for the erbumine salt show a single endothermic event (likely melt or decomposition) beginning at 143.73° C. and three endothermic events (71.17° C., 95.57° C., and 125.15° C.) for the free acid, corresponding to what is likely a hydrate along with at least two anhydrous crystal forms. The thermal characterization data show the erbumine salt has improved thermal stability relative to the free acid and is thermally stable up to at least 100° C.

Hygroscopicity of Treprostinil Erbumine Salt and Sodium Salt

Hygroscopicity analyses of treprostinil erbumine salt, prepared as described above, and treprostinil sodium, purchased from a chemical supply company, are performed on a TA Instruments Q5000SA sorption analyzer. Hygroscopicity profiles are generated on dried samples at 25° C., increasing relative humidity by 5% up to 95%, then decreasing in 5% intervals back down to 5% relative humidity. The samples are equilibrated at each increment until weight percent change is <0.0100 for 5 min.

Figure 3:
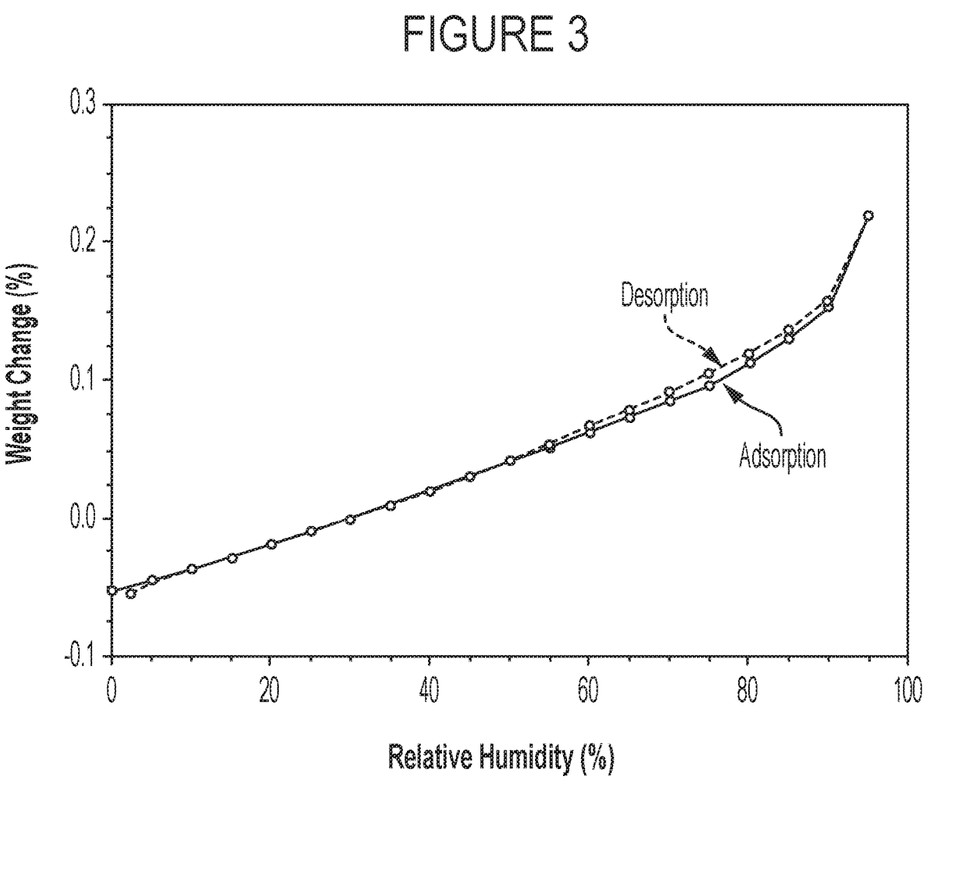
FIG. 3: Dynamic vapor sorption/resorption isotherm of treprostinil erbumine salt.
Figure 4:
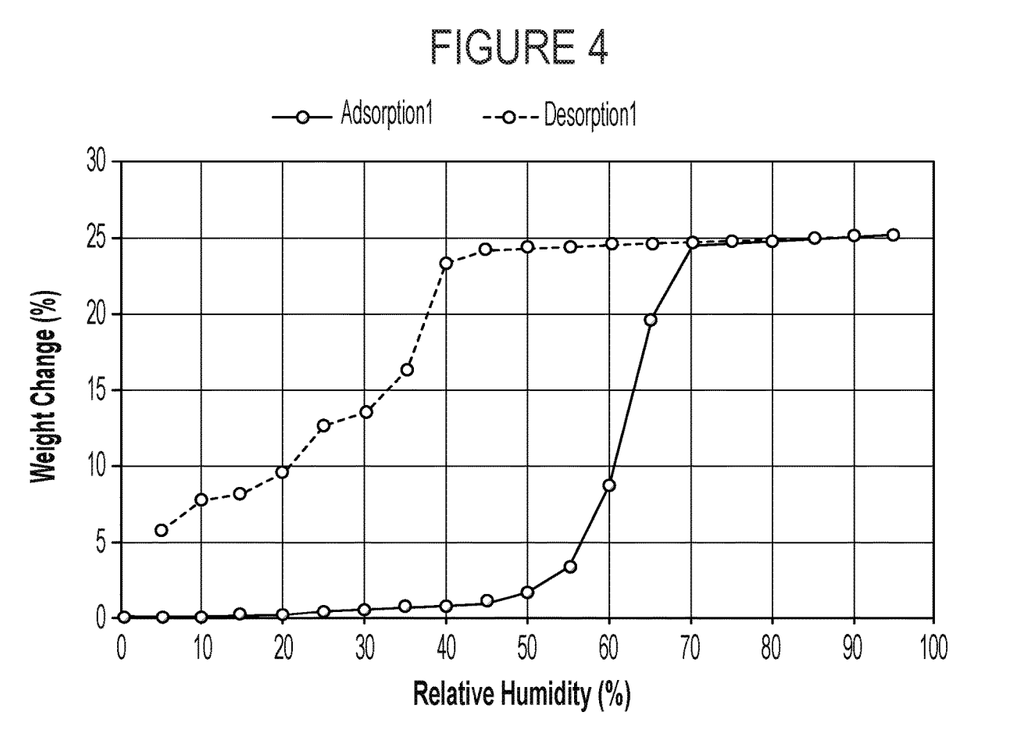
FIG. 4: Dynamic vapor sorption/resorption isotherm of treprostinil sodium salt.

Dynamic vapor sorption/resorption isotherms are provided in FIGS. 3 (erbumine salt) and 4 (sodium salt). For the sodium salt, at the 80% relative humidity point the sample has a 25% weight increase, which is classified as very hygroscopic, and once adsorbed, desorption of water does not appear to begin until relative humidity has decreased to 45% RH. XRD analyses were performed as described above on samples collected at different points in the adsorption/desorption process, and the data show a change in crystal form when the sodium salt is exposed to high relative humidity, followed by a non-reversible change to amorphous or poorly crystalline state when returning to low relative humidity. Surprisingly, on the other hand, for the erbumine salt, at the 80% relative humidity point the weight increase of the sample is <0.2% which is characterized as non-hygroscopic to slightly hygroscopic (as defined in European Pharmacopoeia Online, $9^{th}$ edition, monograph 5.11, though experimental conditions differ from what is therein described). XRD analysis was performed and did not show a physical form change in terms of the amorphization as seen for the sodium salt. These data support the surprising lack of hygroscopicity of the erbumine salt, which allows for improved storage conditions and potency control under ambient conditions. Therefore, both the thermal and moisture sorption data surprisingly show the erbumine salt has significantly improved physical stability relative to the free acid and sodium salt.

I claim:

1. Treprostinil erbumine salt having the following structure:

[Chemical structure of treprostinil erbumine salt]

2. The treprostinil erbumine salt of claim 1 in crystalline form characterized by an XRD pattern obtained from CuKα source ($\lambda$=1.54060 Å) which comprises peaks at 5.1° and at least one of 10.2°, 20.5° and 6.8° with a tolerance for the diffraction angles of 0.2°.

3. The treprostinil erbumine salt of claim 2 wherein the XRD pattern comprises peaks at each of 10.2°, 20.5° and 6.8° with a tolerance for the diffraction angles of 0.2°.

4. The treprostinil erbumine salt of claim 3 wherein the XRD pattern further comprises peaks at least one of 13.7°, 14.5°, 16.3°, 18.7°, 19.6° and 21.5° with a tolerance for the diffraction angles of 0.2°.

5. The treprostinil erbumine salt of claim 3 wherein the XRD pattern further comprises peaks at each of 13.7°, 14.5°, 16.3°, 18.7°, 19.6° and 21.5° with a tolerance for the diffraction angles of 0.2°.

6. A pharmaceutical composition comprising the treprostinil erbumine salt of claim 1 and at least one of a pharmaceutically acceptable carrier, excipient or diluent.

7. The pharmaceutical composition of claim 6 further comprising an additional substance with pharmacological activity.

8. The pharmaceutical composition of claim 7 wherein the additional substance with pharmacological activity is an insulin.

9. The pharmaceutical composition of claim 8 wherein the insulin is insulin lispro.

10. A method of treating or preventing hyperglycemia in a subject in need thereof comprising administering a pharmaceutically effective amount of the pharmaceutical composition of claim 8.

11. A method of treating or preventing hypertension in a subject in need thereof comprising administering a pharmaceutically effective amount of the treprostinil erbumine salt of claim 1.

12. A method of manufacturing the treprostinil erbumine salt of claim 1 comprising:
   a) contacting treprostinil free acid to an antisolvent to create a suspension;
   b) contacting the suspension to a solution comprising t-butylamine (erbumine);
   c) isolating the resulting solid treprostinil erbumine salt.

13. The pharmaceutical composition of claim 8 wherein the insulin is insulin aspart.

14. The pharmaceutical composition of claim 8 wherein the insulin is insulin glulisine.

15. A method of treating or preventing hyperglycemia in a subject in need thereof comprising administering a pharmaceutically effective amount of a pharmaceutical composition comprising:
   treprostinil erbumine salt having the following structure:

, and an insulin.

16. A method of treating ischemic lesions, neuropathic diabetic foot ulcers, interstitial lung disease, asthma, or vasculopathy in a subject in need thereof comprising administering a pharmaceutically effective amount of a pharmaceutical composition according to claim 6.

17. Treprostinil erbumine salt having the following structure:

wherein, the XRD pattern comprises peaks at each of 5.1°, 10.2°, 20.5°, 6.8°, 13.7°, 14.5°, 16.3°, 18.7°, 19.6°, and 21.5° with a tolerance for the diffraction angles of 0.2°.

18. A method of treating or preventing hyperglycemia in a subject in need thereof comprising administering a pharmaceutically effective amount of the pharmaceutical composition of claim 9.

19. A method of treating or preventing hypertension in a subject in need thereof comprising administering a pharmaceutically effective amount of the pharmaceutical composition of claim 6.

* * * * *

UNITED STATES PATENT AND TRADEMARK OFFICE
CERTIFICATE OF CORRECTION

| | | |
|---|---|---|
| PATENT NO. | : 12,102,610 B2 | Page 1 of 1 |
| APPLICATION NO. | : 17/274883 | |
| DATED | : October 1, 2024 | |
| INVENTOR(S) | : David Michael Remick | |

It is certified that error appears in the above-identified patent and that said Letters Patent is hereby corrected as shown below:

In the Claims

In Claim 17, at Column 8, Lines 6-19, insert:

Signed and Sealed this
Twenty-seventh Day of May, 2025

Coke Morgan Stewart
*Acting Director of the United States Patent and Trademark Office*